US008546722B2

(12) United States Patent
Yamada et al.

(10) Patent No.: US 8,546,722 B2
(45) Date of Patent: Oct. 1, 2013

(54) LASER PROCESSING APPARATUS AND PROCESSING METHOD EMPLOYED THEREIN

(75) Inventors: Eiichiro Yamada, Yokohama (JP); Akira Inoue, Yokohama (JP); Koji Nakazato, Yokohama (JP); Hiroshi Kohda, Yokohama (JP); Hitoshi Hatayama, Yokohama (JP); Takemi Hasegawa, Yokohama (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 305 days.

(21) Appl. No.: 13/054,459

(22) PCT Filed: Jun. 18, 2009

(86) PCT No.: PCT/JP2009/061110

§ 371 (c)(1), (2), (4) Date: Mar. 3, 2011

(87) PCT Pub. No.: WO2010/007852

PCT Pub. Date: Jan. 21, 2010

(65) Prior Publication Data

US 2011/0155709 A1 Jun. 30, 2011

(30) Foreign Application Priority Data

Jul. 16, 2008 (JP) ............................... P2008-185175

(51) Int. Cl.
*B23K 26/03* (2006.01)
*H01L 21/02* (2006.01)

(52) U.S. Cl.
USPC ............ 219/121.65; 219/121.66; 219/121.62; 219/121.83

(58) Field of Classification Search
USPC ..................... 362/553, 573, 227; 433/29, 31; 219/121.62, 121.76, 121.83, 121.65, 121.66; 228/180.21, 180.22; 356/237.1
See application file for complete search history.

(56) References Cited

U.S. PATENT DOCUMENTS 5,038,016 A * 8/1991 Robertson et al. ....... 219/121.83
5,382,770 A * 1/1995 Black et al. ............. 219/121.63

FOREIGN PATENT DOCUMENTS

JP 63-108983 A 5/1988
JP 04-007850 A 1/1992
JP 05-335735 A 12/1993
JP 09-216087 A 8/1997
JP 10-314968 A 12/1998
JP 2000-042769 A 2/2000
JP 2004-066266 A 3/2004
JP 2004-322166 A 11/2004
JP 2005-125398 A 5/2005

* cited by examiner

*Primary Examiner* — Samuel M Heinrich
(74) *Attorney, Agent, or Firm* — Venable LLP; Michael A. Sartori; Steven J. Schwarz

(57) ABSTRACT

A laser processing apparatus 1 includes a processing light source 3 emitting processing light; an observation light emitting unit 4 emitting observation light; optical fibers 19 conducting light having a plurality of wavelengths generated at an electronic component 2; a detecting unit 5 detecting the light conducted by the optical fibers 19; and a control unit 31 controlling a light emitting state of the processing light emitting unit 3. The optical fibers 19 are categorized into four groups, and disposed so as to surround an optical fiber 18 conducting the processing light. The optical fibers 19 categorized into the four groups are capable of conducting the observation light to the electronic component 2 every group.

19 Claims, 9 Drawing Sheets

1
31
CONTROL UNIT
7 8
3 4 5 13 14
PROCESSING LIGHT SOURCE
FIRST OBSERVATION LIGHT SOURCE
SECOND OBSERVATION LIGHT SOURCE
DETECTING ELEMENT
6 9 10 16 15
MULTIPLEXING UNIT
11
12
17
2

1
31
CONTROL UNIT
7
8
3
4
5
13
14
PROCESSING LIGHT SOURCE
FIRST OBSERVATION LIGHT SOURCE
SECOND OBSERVATION LIGHT SOURCE
DETECTING ELEMENT
6
9
10
16
15
11
MULTIPLEXING UNIT
12
17
2

(a)

(b)

26
31
CONTROL UNIT
3
27
28
22
PROCESSING LIGHT SOURCE
DETECTING ELEMENT
OBSERVATION LIGHT SOURCE
29
6
25
24
30
2

LASER PROCESSING APPARATUS AND PROCESSING METHOD EMPLOYED THEREIN

TECHNICAL FIELD

The present invention relates to a laser processing apparatus and a processing method employed therein.

BACKGROUND ART

An example of conventional technology in the field is disclosed in Patent Literature 1. A laser processing apparatus disclosed in the literature has a laser light source emitting bonding light to a bonding portion of a lead and a bonding land of a substrate; another laser light source emitting determining light; a determination apparatus determining the bonding state of the bonding portion; and a CCD camera identifying a defect of the lead. The bonding portion is irradiated with the bonding light, and then irradiated with the determining light. Reflected light and radiant light from the determining light are received at the determination apparatus, which then determines the bonding state. Furthermore, the CCD camera identifies a defective lead, thus enhancing the reliability of mounting.

CITATION LIST

Patent Literature

Patent Literature 1: Japanese Unexamined Patent Application Publication No. 5-335735

SUMMARY OF INVENTION

Technical Problem

The conventional laser processing apparatus, however, is not provided with a means identifying an adjacent object disposed in the vicinity of the bonding portion, a means controlling irradiation power with the bonding light according to the type of the adjacent object, for example. Such an apparatus may erroneously process the adjacent object, failing to improve processing accuracy.

An object of the present invention is to provide a laser processing apparatus and a laser processing method having high processing accuracy.

Solution to Problem

The present invention provides a laser processing apparatus scanning and processing an object to be processed with processing light. The laser processing apparatus includes a first light emitting unit emitting processing light; a first light guide conducting the processing light emitted from the first light emitting unit to an object to be processed; a second light emitting unit emitting observation light that observes the object to be processed; a plurality of second light guides conducting the observation light emitted from the second light emitting unit to the object to be processed; a third light guide conducting light having a plurality of wavelengths generated at the object to be processed; a detecting unit detecting the light having a plurality of wavelengths conducted by the third light guide; and a control unit controlling a light emitting state of the first light emitting unit, based on a result of detection by the detecting unit. The second light guides are categorized into at least two groups, and conduct the observation light to the object to be processed every group, the observation light being emitted from the second light emitting unit.

According to the laser processing apparatus of the present invention, the second light guides are categorized into at least two groups, and conduct the observation light to the object to be processed every group, the observation light being emitted from the second light emitting unit. Thus, differentiating a radiation timing of the observation light emitted from each group allows identification of an object to be irradiated respectively with the observation light emitted every group. In addition, a position of the identified object corresponds to a disposed position of each group. The position of the identified object can thus be easily determined, based on the disposed position of the group. Accordingly, it is possible to control radiation power of the processing light according to the type of the identified object, or to adjust a radiation time of the processing light according to the position of the identified object. This can prevent the identified object from being processed erroneously, and thus can enhance processing accuracy.

It is preferred in the laser processing apparatus according to the present invention that the second light guides are categorized into four groups; and that, at an emission end of the first light guide, the second light guides categorized into the four groups are disposed a forward direction, a backward direction, left hand, and right hand relative to a scanning direction of the processing light emitted from the first light guide, such that the second light guides surround the first light guide. Thereby, objects disposed in the forward direction, backward direction, left hand, and right hand to the processed area can be identified respectively.

It is preferred in the laser processing apparatus according to the present invention that the second light guides categorized into the four groups, in sequence, conduct the observation light emitted from the second light emitting unit to the object to be processed. Thereby, an object disposed in the forward direction, backward direction, left hand, and right hand to the processed area can easily be identified.

The present invention provides a laser processing apparatus scanning and processing an object to be processed with processing light. The laser processing apparatus includes a first light emitting unit emitting processing light; a first light guide conducting the processing light emitted from the first light emitting unit to an object to be processed; a second light emitting unit emitting observation light that observes the object to be processed; a second light guide conducting the observation light emitted from the second light emitting unit to the object to be processed; a plurality of third light guides conducting light having a plurality of wavelengths generated at the object to be processed; a detecting unit detecting the light having a plurality of wavelengths conducted by the third light guides; and a control unit controlling a light emitting state of the first light emitting unit, based on a result of detection by the detecting unit. The third light guides are categorized into at least two groups, and conduct the light every group, the light having a plurality of wavelengths generated at the object to be processed.

According to the laser processing apparatus of the present invention, the third light guides are categorized into at least two groups, and conduct the light every group, the light having a plurality of wavelengths generated at the object to be processed. Thus, differentiating a timing to conduct the light by each group allows identification of an object corresponding to the third light guides of each group respectively. In addition, a position of the identified object corresponds to a disposed position of each group. The position of the identified object can thus be easily determined, based on the disposed position of the group. Accordingly, it is possible to control radiation power of the processing light according to the type of the identified object, or to adjust a radiation time of the processing light according to the position of the identified object. This can prevent the identified object from being processed erroneously, and thus can enhance processing accuracy.

It is preferred in the laser processing apparatus according to the present invention that the third light guides are categorized into four groups; and that, at an emission end of the first light guide, the third light guides categorized into the four groups are disposed a forward direction, a backward direction, left hand, and right hand relative to a scanning direction of the processing light emitted from the first light guide, such that the third light guides surround the first light guide. Thereby, objects disposed in the forward direction, backward direction, left hand, and right hand to the processed area can be identified respectively.

It is preferred in the laser processing apparatus according to the present invention that the third light guides categorized into the four groups, in sequence, conduct the light having a plurality of wavelengths generated at the object to be processed. Thereby, an object disposed over the forward direction, backward direction, left hand, and right hand to the processed area can easily be identified.

It is preferred in the laser processing apparatus according to the present invention that the detecting unit includes a detecting element corresponding to each group of the third light guides. This enhances accuracy of the light detection.

It is preferred in the laser processing apparatus according to the present invention that the detecting unit includes a single detecting element and light path changing means allowing the light conducted by the third light guides to enter the detecting element. This can simplify a configuration of the detecting unit, and thus can reduce cost of the apparatus as a whole.

The present invention provides a laser processing method using the laser processing apparatus described above. The laser processing method includes (1) irradiating the object to be processed with the observation light from every group of the second light guides; (2) detecting the light having a plurality of wavelengths generated at the object to be processed, and identifying the object as an object to be irradiated or not, based on properties of the detected light; and (3) controlling the processing light based on a result of identification of the object to be irradiated, and processing the object.

According to the laser processing method of the present invention, the object to be processed is irradiated with the observation light from every group of the second light guides, and thereby the type and position of the object disposed in the vicinity of the processed area can easily be specified. It is then possible to control radiation power of the processing light according to the type of the identified object, or to adjust a radiation time of the processing light according to the position of the identified object. This can prevent the identified object from being processed erroneously, and thus can enhance processing accuracy.

It is preferred in the laser processing method according to the present invention that, in step (1), the group of the second light guides disposed forward in the scanning direction of the processing light is used alone to radiate the observation light onto the object to be processed. This identifies an object disposed forward in the scanning direction of the processing light alone, and thus can contribute to an increased processing speed.

The present invention provides a laser processing method using the laser processing apparatus described above. The laser processing method includes (1) irradiating the object to be processed with the observation light; (2) detecting the light having a plurality of wavelengths generated at the object to be processed, using each group of the third light guides, and identifying the object as an object to be irradiated or not, based on properties of the detected light; and (3) controlling the processing light based on a result of identification of the object to be irradiated, and processing the object.

According to the laser processing method of the present invention, the light having a plurality of wavelengths generated at the object to be processed is detected by each group of the third light guides, and thereby the type and position of the object disposed in the vicinity of the processed area can easily be specified. It is then possible to control radiation power of the processing light according to the type of the identified object, or to adjust a radiation time of the processing light according to the position of the identified object. This can prevent the identified object from being processed erroneously, and thus can enhance processing accuracy.

It is preferred in the laser processing method according to the present invention that, in step (2), the group of the third light guides disposed forward in the scanning direction of the processing light is used alone to detect the light having a plurality of wavelengths generated at the object to be processed. This identifies an object disposed forward in the scanning direction of the processing light alone, and thus can contribute to an increased processing speed.

Advantageous Effects of Invention

The present invention provides the laser processing apparatus and the laser processing method capable of enhancing processing accuracy.

BRIEF DESCRIPTION OF DRAWINGS

FIG. 2(*b*) illustrates grouping of optical fibers;

DESCRIPTION OF EMBODIMENTS

Figure 1:
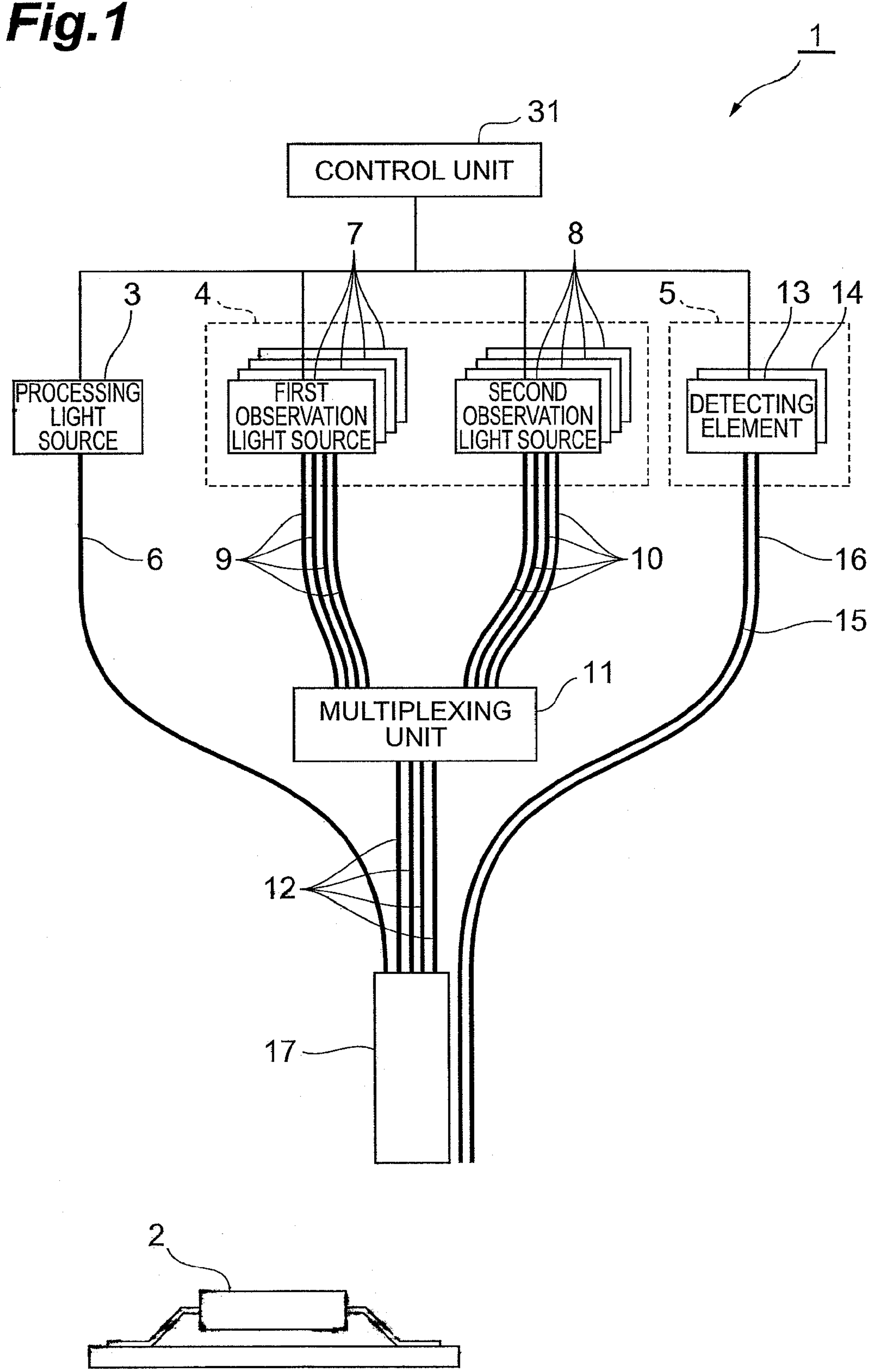
FIG. 1 is a schematic view illustrating a configuration of a laser processing apparatus according to a first embodiment.

Preferred embodiments to implement the present invention are explained in detail below, with reference to the attached drawings. In the explanation of the drawings, the same reference numerals are assigned to the same elements, and duplicated explanation is omitted to avoid redundancy.

First Embodiment

FIG. 1 is a schematic view illustrating a configuration of a laser processing apparatus according to a first embodiment. A laser processing apparatus 1, which is used for processing electronic components, has a processing light source (first light emitting unit) 3 emitting processing light to process an electronic component (object to be processed) 2; an observation light emitting unit (second light emitting unit) 4 emitting observation light to observe the electronic component 2; a detecting unit 5 detecting light having a plurality of wavelengths generated at the electronic component 2; and a control unit 31 controlling a light emitting state of the processing light source 3.

The processing light source 3 includes a semiconductor laser element outputting laser light having a specific wavelength of 408 nm. The processing light emitted from the processing light source 3 is conducted to the electronic component 2 by an optical fiber (first light guide) 6 optically connected to the processing light source 3.

The observation light emitting unit 4, which emits the observation light to observe the electronic component 2, has two types of light sources having different central wavelengths. Specifically, the observation light emitting unit 4 includes four first observation light sources 7 outputting laser light having a wavelength of 445 nm, and four second observation light sources 8 outputting laser light having a wavelength of 660 nm. The four first observation light sources 7 are optically connected to four optical fibers (second light guides) 9; and the four second observation light sources 8 are optically connected to four optical fibers (second light guides) 10.

The optical fibers 9 and 10 are also connected to a multiplexing unit 11. The multiplexing unit 11 multiplexes the light having a wavelength of 445 nm conducted by the optical fibers 9 and the light having a wavelength of 660 nm conducted by the optical fibers 10 at a ratio of one to one, and then outputs the multiplexed light to the electronic component 2 by way of four optical fibers (second light guides) 12.

The detecting unit 5 is provided with a first detecting element 13 and a second detecting element 14, which have different light-receiving sensitivities depending on the wavelength. The first detecting element 13 has a high light-receiving sensitivity to light having a wavelength of 445 nm; and the second detecting element 14 has a high light-receiving sensitivity to light having a wavelength of 660 nm. The first detecting element 13 and the second detecting element 14 are optically connected to optical fibers (third light guides) 15 and 16, respectively. The first detecting element 13 and the second detecting element 14 detect the intensity of different wavelengths of light conducted by the optical fibers 15 and 16, respectively, and output the results of detection to the control unit 31. The detecting unit 5 may be provided with an optical filter and a plurality of detecting elements, the optical filter transmitting or reflecting light having different center wavelengths, the detecting elements detecting the intensity of the light which has been transmitted or reflected by the optical filter and has different center wavelengths. Alternatively, the detecting unit 5 may be provided with a light path changing means and detecting elements, the light path changing means separating or switching the light path from the third light guide to the detecting element according to the wavelength, the detecting elements corresponding to light travelling through the respective light paths.

The control unit 31 controls the light emitting state of the processing light source 3, based on the results detected by the first detecting element 13 and the second detecting element 14. Furthermore, the control unit 31 calculates the ratio of the light intensity of a wavelength of 445 nm detected by the first detecting element 13 and the light intensity of a wavelength of 660 nm detected by the second detecting element 14. The control unit 31 then compares the computed value with a reference threshold value, and thereby identifies an object on the electronic component 2.

The optical fibers 6 and the optical fibers 12 are bundled at the emission end of the optical fibers 6 into a bundle fiber 17. Bundling the optical fibers 6 and 12 allows downsizing of the laser processing apparatus 1 and easy operation of the apparatus. It is also preferred that a collecting lens (not shown in the drawing) be installed at an end of the bundle fiber. This ensures a long operating distance to the object to be processed and facilitates operation of the apparatus.

Figure 2:
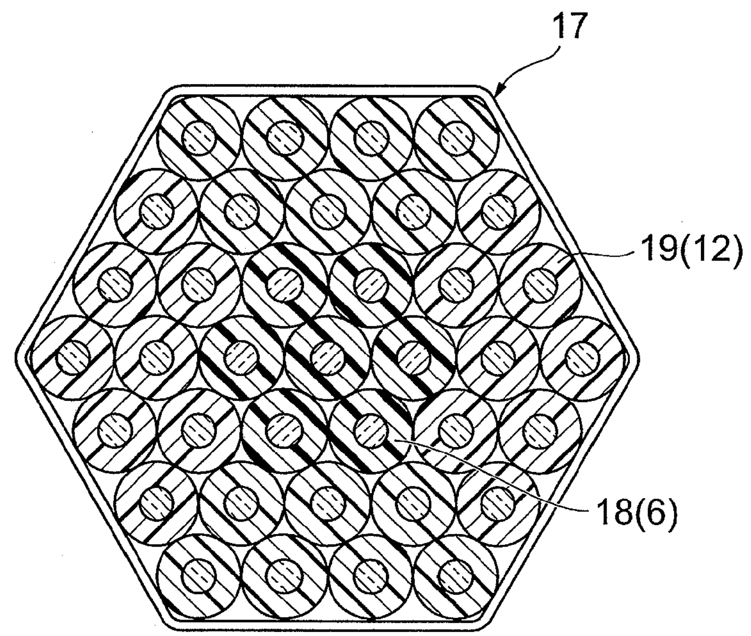
FIG. 2(*a*) is a cross-sectional view of a bundle fiber.
Figure 2:
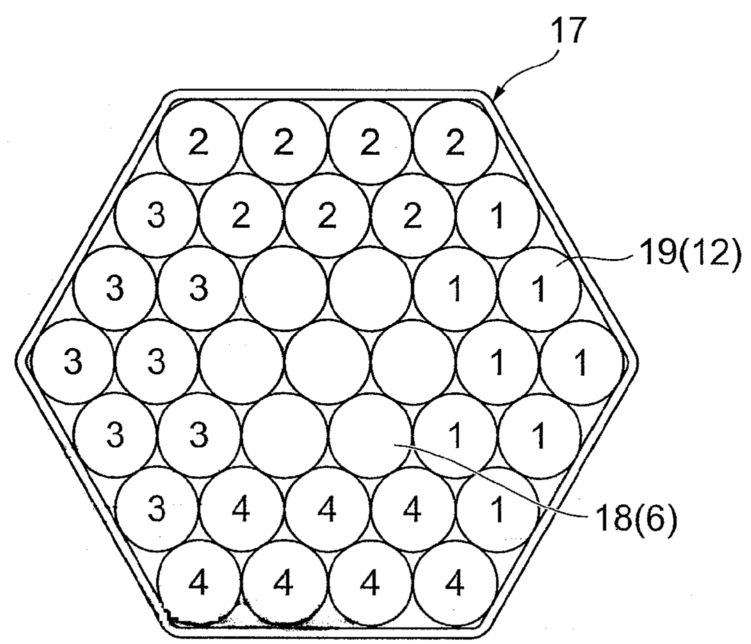

FIG. 2(*a*) is a cross-sectional view of the bundle fiber; and FIG. 2(*b*) illustrates grouping of optical fibers. As shown in FIG. 2(*a*), the bundle fiber 17 has a hexagonal cross-section. Seven optical fibers (first light guides) 18 are provided in the central portion of the bundle fiber 17. Thirty optical fibers (second light guides) 19 are disposed surrounding the optical fibers 18. The seven optical fibers 18 function as the optical fibers 6 that conduct the processing light. The thirty optical fibers 19 function as the optical fibers 12 that conduct the observation light.

As shown in FIG. 2(*b*), the thirty optical fibers 19 are categorized into four groups corresponding to the four optical fibers 12. A first group includes eight optical fibers 19; a second group includes seven optical fibers 19; a third group includes eight optical fibers 19; and a fourth group includes seven optical fibers 19.

Figure 3:
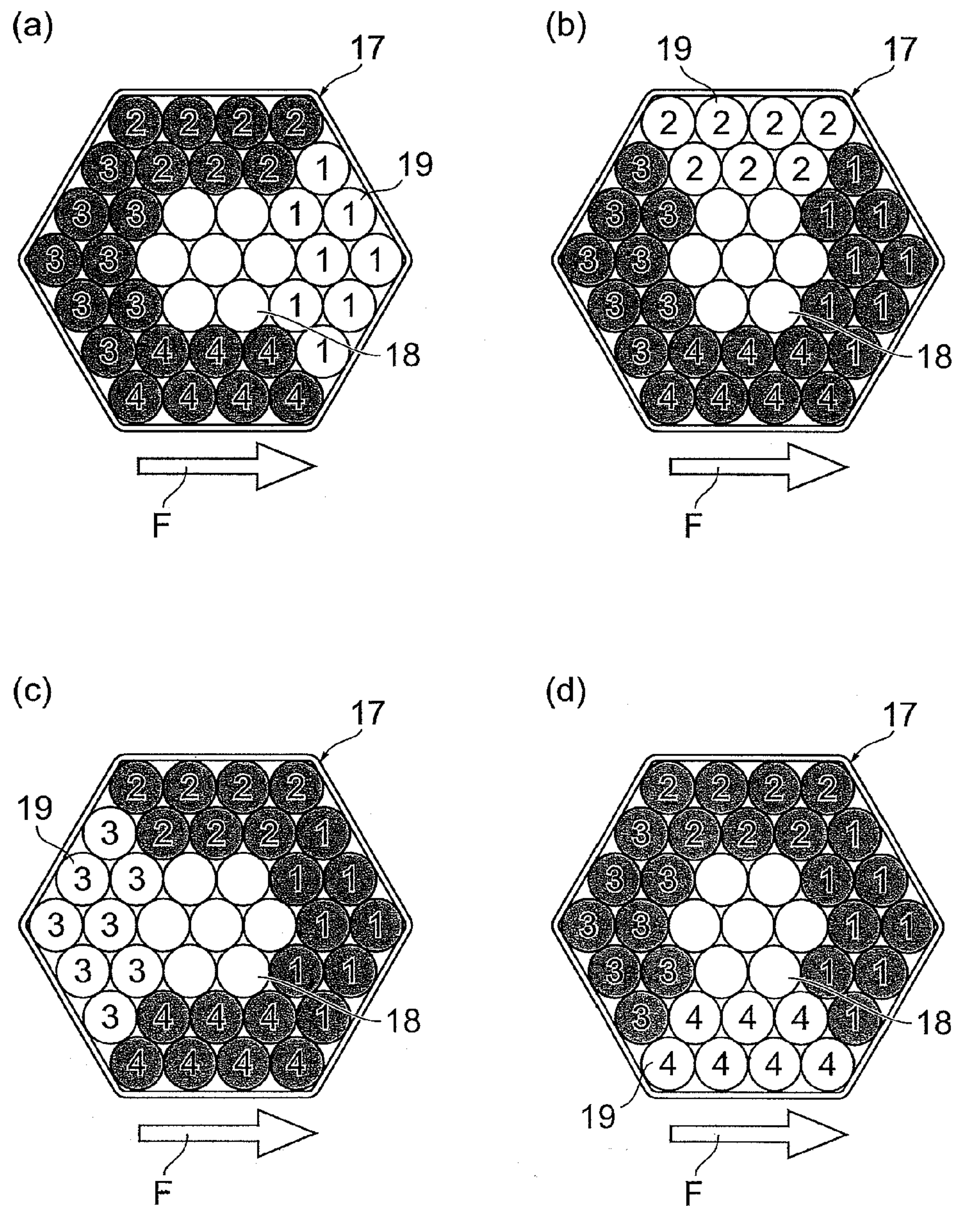
FIGS. 3(*a*) to 3(*d*) illustrate a radiation timing of observation light emitted from each group of the optical fibers.

The optical fibers 19 categorized into the four groups are provided, such that the observation light can be conducted toward the electronic component 2 every group. For instance, the optical fibers 19 categorized into the four groups receive a control signal from the control unit 31, and conduct the observation light in the order of the first, second, third, and fourth groups. FIGS. 3(*a*) to 3(*d*) illustrate a radiation timing of the observation light emitted from each group of the optical fibers. In FIGS. 3(*a*) to 3(*d*), white circles represent a state in which the observation light emitted from the optical fibers 19 is radiated; and solid black circles represent a state in which the observation light is not radiated.

In FIGS. 3(*a*) to 3(*d*), an arrow F represents a scanning direction of the processing light. The optical fibers 19 of the first, second, third, and fourth groups are thus disposed the forward direction, left hand, backward direction, and right hand relative to the scanning direction F. As shown in FIG. 3(*a*), the electronic component 2 is scanned and processed with the processing light conducted by the optical fibers 18, and concurrently irradiated with the observation light emitted from the optical fibers 19 of the first group alone for a predetermined period of time. Then, the irradiation with the observation light emitted from the optical fibers 19 of the first group is stopped, and the observation light emitted from the optical fibers 19 of the second group alone is radiated onto the electronic component 2 for a predetermined period of time (refer to FIG. 3(*b*)).

Subsequently, the irradiation with the observation light emitted from the optical fibers 19 of the second group is stopped, and the observation light emitted from the optical fibers 19 of the third group alone is radiated onto the electronic component 2 for a predetermined period of time (refer to FIG. 3(*c*)). Then, the irradiation with the observation light emitted from the optical fibers 19 of the third group is stopped, and the observation light emitted from the optical fibers 19 of the fourth group alone is radiated onto the electronic component 2 for a predetermined period of time (refer to FIG. 3(*d*)). These operations are repeated until the processing ends.

In the laser processing apparatus having such a configuration, the optical fibers 19 are categorized into the four groups, and the observation light emitted from the observation light emitting unit 4 is conducted every group to the electronic component 2. Thus, sequentially conducting and radiating the observation light emitted from the groups onto the electronic component 2 allows identification of an object on the electronic component 2 (a gilded terminal, a tinned terminal, and a glass epoxy substrate, for instance) which is irradiated with the observation light emitted every group.

In addition, a position of the identified object corresponds to a disposed position of each group of the optical fibers 19. The position of the identified object can thus be easily determined, based on the disposed position of the group. Accordingly, it is possible to control radiation power of the processing light according to the type of the identified object, or to adjust a radiation time of the processing light according to the position of the identified object. For example, in order to bond gilded terminals with solder (tin-based) by scanning with the processing light, a boundary of the solder and the gilded terminals can be specified and the radiation power can be intensified. This can prevent the electronic component 2 from being overheated, and thus can enhance processing accuracy and quality.

Figure 4:
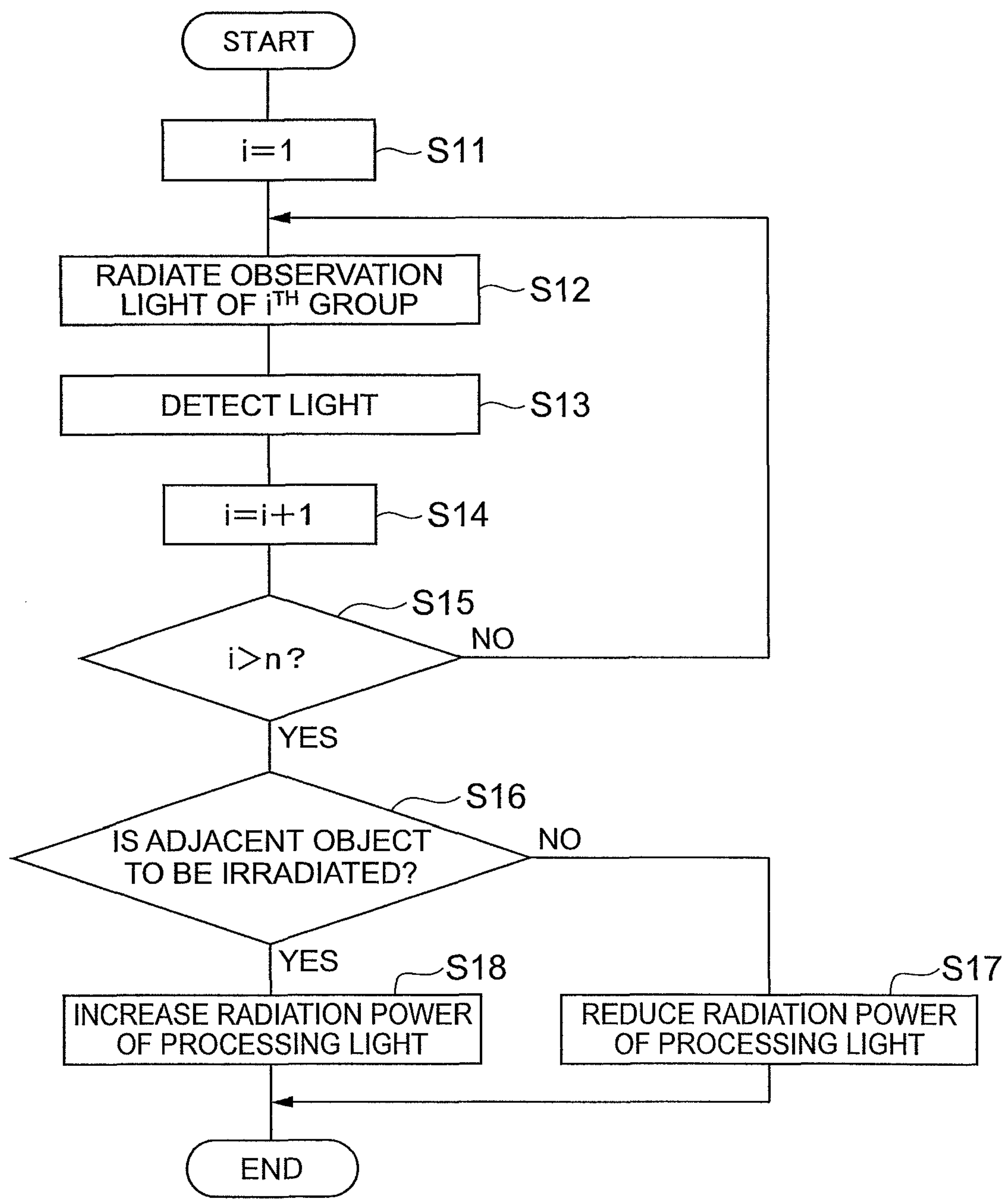
FIG. 4 is a flowchart illustrating a control process of the laser processing apparatus according to the first embodiment.

A laser processing method using the laser processing apparatus 1 according to the first embodiment is explained below, with reference to FIG. 4. FIG. 4 is a flowchart illustrating a control process of the laser processing apparatus according to the first embodiment. The control process in FIG. 4 is repeated by the control unit 31 at a predetermined cycle.

The group number i is first set to 1 (S11). The observation light emitted from the optical fibers 19 of the $i^{th}$ (i=1) group is radiated onto the electronic component 2 (S12). Then, light generated at the electronic component 2 by the irradiation with the observation light is detected (S13). In the process, the light having a plurality of wavelengths generated on the electronic component 2 is detected through the optical fibers 15 and 16 and the detecting elements 13 and 14; and an adjacent object proximate to the processed area is then identified based on properties of the detected light.

Subsequently, 1 is added to the original group number i, and a new group number i is set (S14). The group number i is compared with a reference value n (S15). If the group number i is equal to or less than the reference value n, the process returns to S12. If the group number i is greater than the reference value n, it is determined whether or not the adjacent object is an object to be irradiated (S16).

The optical fibers 19 are categorized into the four groups in the laser processing apparatus 1, as described above. Thus, in the case where the reference value n is 4, the observation light emitted from the optical fibers 19 of the first, second, third, and fourth groups is radiated in sequence.

If it is determined in S16 that the adjacent object is not to be irradiated, the irradiation power with the processing light is reduced in a process proceeding to the next point (S17). In the process, the control unit 31 transmits, to the processing light source 3, a control signal to reduce the irradiation power; and the processing light source 3 receives the control signal and reduces the power of the generated processing light.

If it is determined that the adjacent object is to be irradiated, the irradiation power with the processing light is increased in a process proceeding to the next point (S18). In the process, the control unit 31 transmits, to the processing light source 3, a control signal to increase the irradiation power; and the processing light source 3 receives the control signal and increases the power of the generated processing light. Thereby, the electronic component 2 is processed. After the process of S17 or S18 is completed, the processes are repeated at the next point. A series of the control process ends in such a way.

According to such a laser processing method, irradiation of the electronic component 2 with the observation light from each group of the optical fibers 19 enables the adjacent object in the processed area to be identified easily. It is then determined whether the adjacent object is to be irradiated. The irradiation power with the processing light is increased or reduced based on the determination. This can prevent the adjacent object from being processed by error. Consequently, the processing accuracy can be improved.

Figure 5:
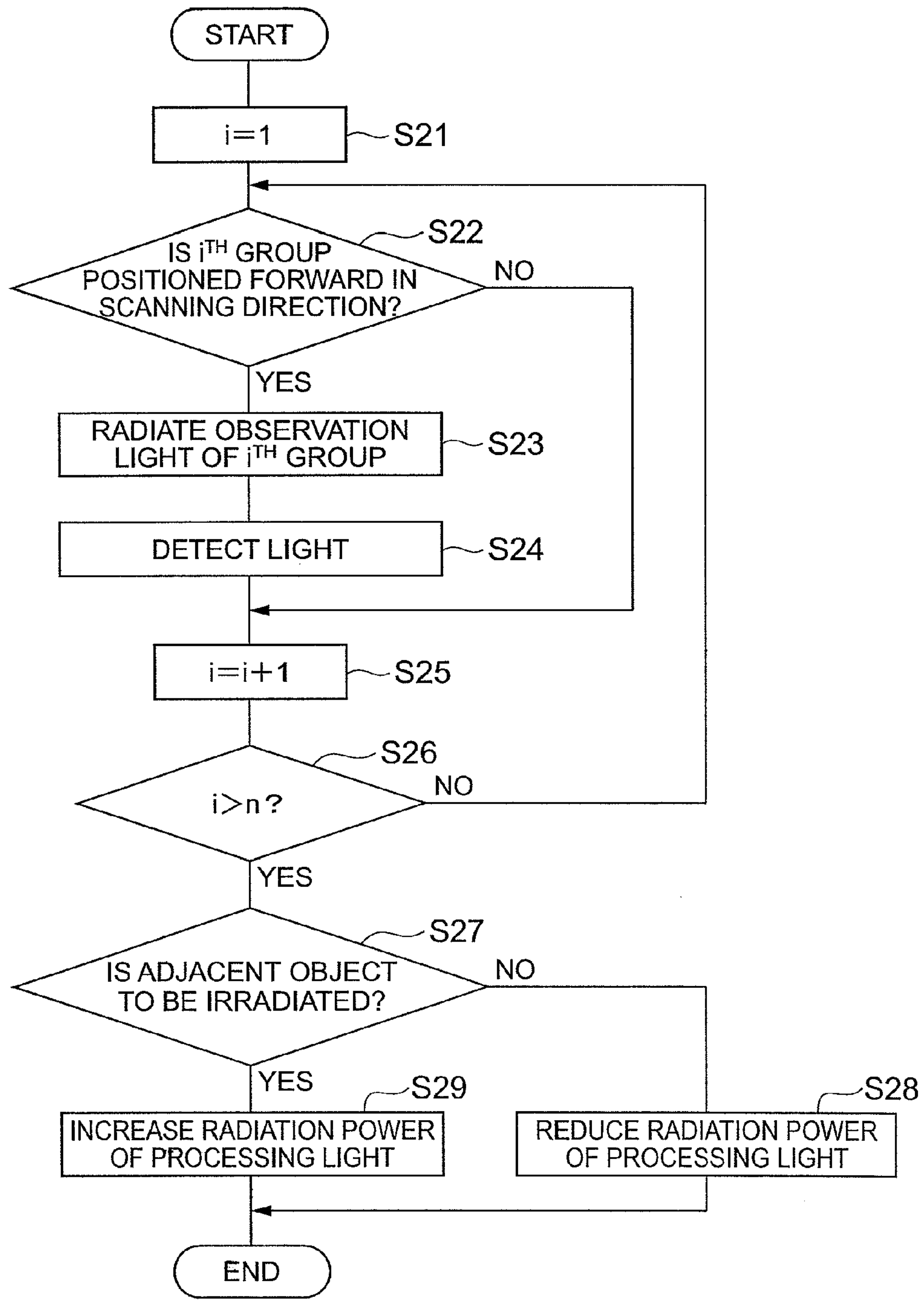
FIG. 5 is a flowchart illustrating a control process of the laser processing apparatus according to the first embodiment.

An alternative processing method using the laser processing apparatus 1 is explained below with reference to FIG. 5. FIG. 5 is a flowchart illustrating a control process of the laser processing apparatus according to the first embodiment. The control process in FIG. 5 is characterized in that, among the optical fibers 19, the group disposed forward in the scanning direction of the processing light is used alone to radiate the observation light. The control process is repeated by the control unit 31 at a predetermined cycle.

The group number i is first set to 1 (S21). It is then determined whether or not the $i^{th}$ (i=1) group is positioned forward in the scanning direction of the processing light (S22). If it is determined that the group is not positioned forward in the scanning direction, the observation light emitted from the optical fibers 19 of the group is not radiated, and the process proceeds to S25. If it is determined that the group is positioned forward in the scanning direction, the observation light emitted from the optical fibers 19 of the group is radiated (S23).

Then, light generated at the electronic component 2 by the irradiation with the observation light is detected (S24). In the process, the light having a plurality of wavelengths generated at the electronic component 2 is detected through the optical fibers 15 and 16 and the detecting elements 13 and 14; and an adjacent object is then identified based on properties of the detected light.

Subsequently, 1 is added to the original group number i, and thus a new group number i is set (S25). The group number i is compared with a reference value n (S26). If the group number i is equal to or less than the reference value n, the process returns to S22. If the group number i is greater than the reference value n, it is determined whether or not the adjacent object is an object to be irradiated (S27).

If it is determined in S27 that the adjacent object is not to be irradiated, the irradiation power with the processing light is reduced in a process proceeding to the next point (S28). In the process, the control unit 31 transmits, to the processing light source 3, a control signal to reduce the irradiation power; and the processing light source 3 receives the control signal and reduces the power of the generated processing light.

If it is determined that the adjacent object is to be irradiated, the irradiation power with the processing light is increased in a process proceeding to the next point (S29). In the process, the control unit 31 transmits, to the processing light source 3, a control signal to increase the irradiation power; and the processing light source 3 receives the control signal and increases the power of the generated processing light. Thereby, the electronic component 2 is processed. After the process of S28 or S29 is completed, a series of the control process ends. The laser processing method, which identifies only the adjacent object positioned forward in the scanning direction of the processing light, contributes to an increased processing speed.

Second Embodiment

Figure 6:
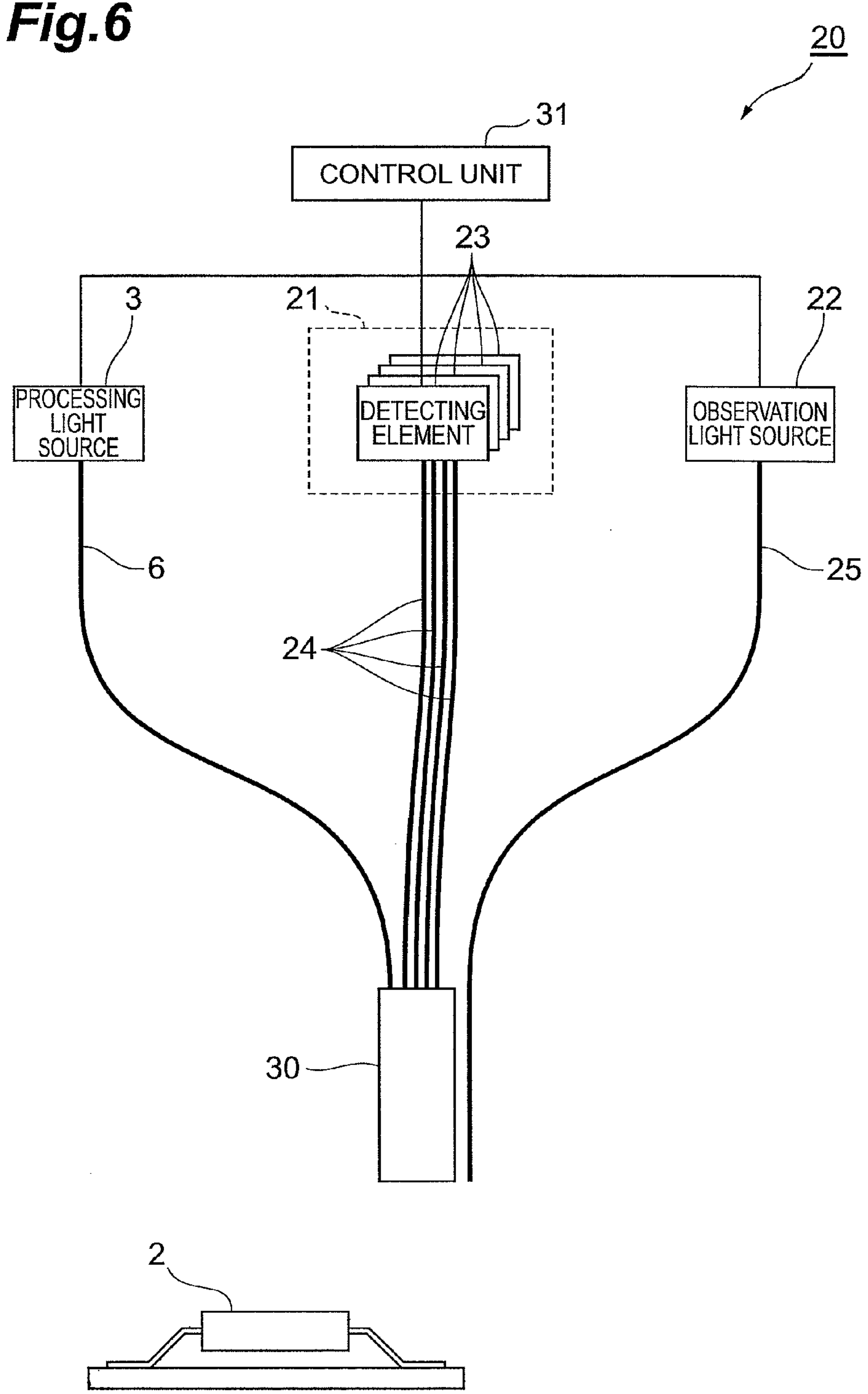
FIG. 6 is a schematic view illustrating a configuration of a laser processing apparatus according to a second embodiment.

A laser processing apparatus 20 according to a second embodiment is explained below. FIG. 6 is a schematic view illustrating a configuration of the laser processing apparatus according to the second embodiment. The laser processing apparatus 20 according to the second embodiment is different from the first embodiment in that optical fibers (third light guides) 24 conducting light generated at the electronic component 2 are categorized into four groups. Other components of the configuration are equivalent to those of the laser processing apparatus 1 described above. Thus, the same reference numerals are assigned, and duplicated explanation is omitted to avoid redundancy.

As shown in FIG. 6, a detecting unit 21 has four detecting elements 23. The detecting elements 23 detect light having a plurality of wavelengths, including a wavelength of 445 nm and a wavelength of 660 nm. The four detecting elements 23 are optically connected to the four respective optical fibers 24. Furthermore, the laser processing apparatus 20 has a single observation light source (second light emitting unit) 22. The observation light source 22 includes a halogen lamp emitting white light. The observation light emitted from the observation light source 22 is radiated onto the electronic component 2 through an optical fiber 25 (second light guide).

The optical fibers 6 and the optical fibers 24 are bundled at the emission end of the optical fibers 6 into a bundle fiber 30. The bundle fiber 30 has a configuration similar to the bundle fiber 17 of the first embodiment. Specifically, the optical fibers 24 conducting light generated at the electronic component 2 are categorized into four groups; and disposed the forward direction, backward direction, left hand, and right hand relative to the scanning direction of the processing light, such that the optical fibers 24 surround the optical fibers 6 conducting the processing light. It is also preferred that a collecting lens (not shown in the drawing) be installed at an end of the bundle fiber. This ensures a long operating distance to the object to be processed and facilitates operation of the apparatus.

The optical fibers 24 categorized into the four groups are provided, such that the light having a plurality of wavelengths generated at the electronic component 2 can be conducted in sequence. For instance, an openable/closable mask corresponding to each group is provided between the optical fibers 24 categorized into the four groups and the detecting elements 23. Opening or closing the mask allows the light conducted by the optical fibers 24 to enter the detecting elements 23 or blocks the light in sequence.

In the laser processing apparatus 20 having such a configuration, the optical fibers 24 are categorized into the four groups, and the light having a plurality of wavelengths generated at the electronic element 2 is conducted every group. Thus, differentiating a timing to conduct the light by each group allows identification of an object corresponding to the optical fibers 24 of each group (a gilded terminal, a tinned terminal, and a glass epoxy substrate, for instance).

In addition, a position of the identified object corresponds to a disposed position of each group of the optical fibers 24. The position of the identified object can thus be easily determined, based on the disposed position of the group. Accordingly, it is possible to control radiation power of the processing light according to the type of the identified object, or to adjust a radiation time of the processing light according to the position of the identified object. For example, in order to bond gilded terminals with solder (tin-based) by scanning with the processing light, a boundary of the solder and the gilded terminals can be specified and the radiation power can be intensified. This can prevent the electronic component 2 from being overheated, and thus can enhance processing accuracy and quality.

Figure 7:
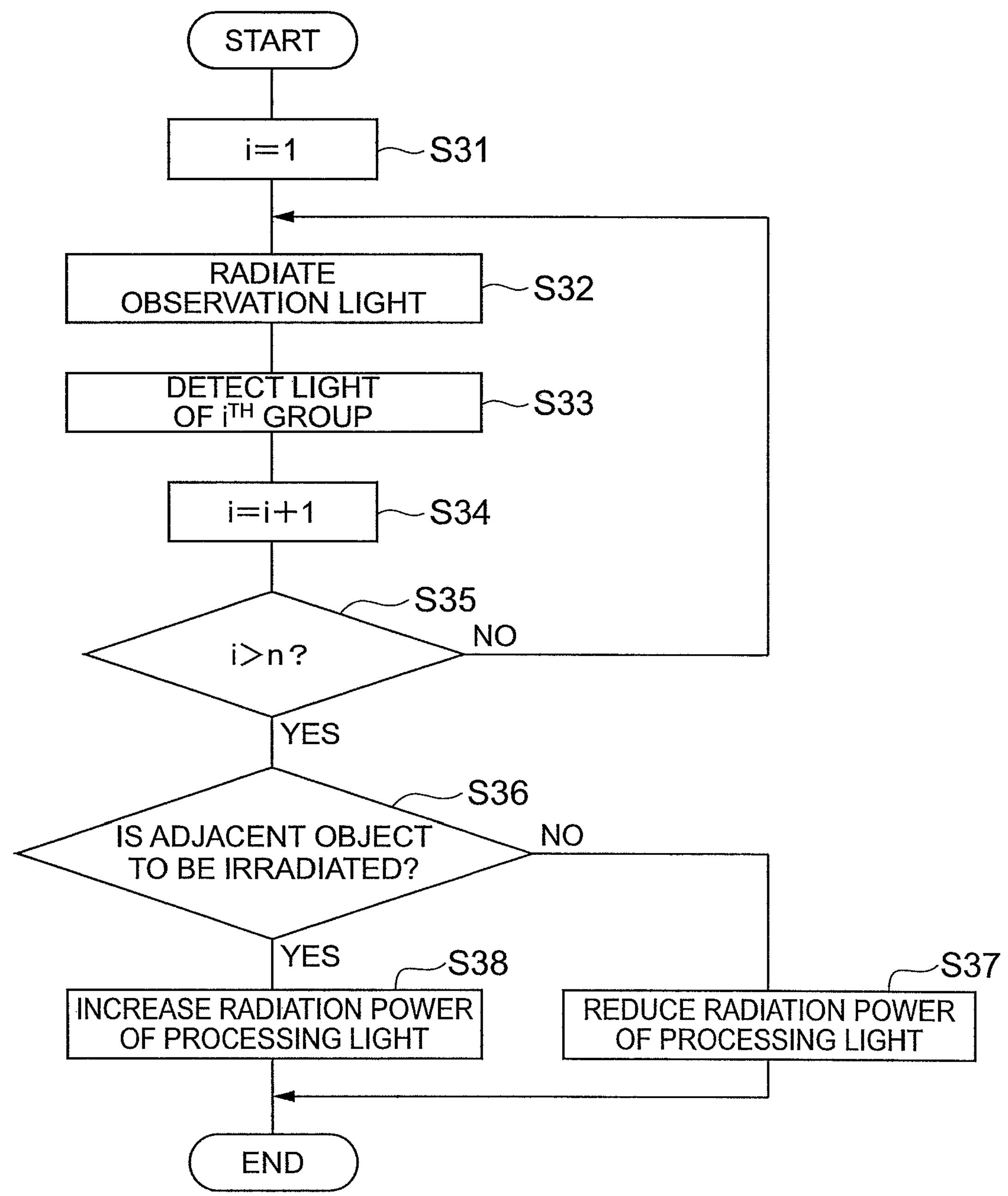
FIG. 7 is a flowchart illustrating a control process of the laser processing apparatus according to the second embodiment.

A laser processing method using the laser processing apparatus 20 according to the second embodiment is explained below, with reference to FIG. 7. FIG. 7 is a flowchart illustrating a control process of the laser processing apparatus according to the second embodiment. The control process in FIG. 7 is repeated by the control unit 31 at a predetermined cycle.

The group number i is first set to 1 (S31). The observation light emitted from the optical fiber 25 is radiated onto the electronic component 2 (S32). Then, light generated at the electronic component 2 by the irradiation with the observation light is detected (S33). In the process, the light having a plurality of wavelengths generated on the electronic component 2 is detected through the optical fibers 24 of the $i^{th}$ (i=1) group and the detecting element 23 thereof; and an adjacent object proximate to the processed area is then identified based on properties of the detected light.

Subsequently, 1 is added to the original group number i, and a new group number i is set (S34). The group number i is compared with a reference value n (S35). If the group number i is equal to or less than the reference value n, the process returns to S32. If the group number i is greater than the reference value n, it is determined whether or not the adjacent object is an object to be irradiated (S36).

The optical fibers 24 are categorized into the four groups in the laser processing apparatus 20. Thus, at a reference value n of 4, for example, the light through the optical fibers 24 of the first, second, third, and fourth groups is detected in sequence.

If it is determined in S36 that the adjacent object is not to be irradiated, the irradiation power with the processing light is reduced in a process proceeding to the next point (S37). In the process, the control unit 31 transmits, to the processing light source 3, a control signal to reduce the irradiation power; and the processing light source 3 receives the control signal and reduces the power of the generated processing light.

If it is determined that the adjacent object is to be irradiated, the irradiation power with the processing light is increased in a process proceeding to the next point (S38). In the process, the control unit 31 transmits, to the processing light source 3, a control signal to increase the irradiation power; and the processing light source 3 receives the control signal and increases the power of the generated processing light. Thereby, the electronic component 2 is processed. After the process of S37 or S38 is completed, the processes are repeated at the next point. A series of the control process ends in such a way.

According to such a laser processing method, detecting the light generated at the electronic component 2 through each group of the optical fibers 24 enables the adjacent object in the processed area to be identified easily. It is then determined whether the adjacent object is to be irradiated. The irradiation power with the processing light is increased or reduced based on the determination. This can prevent the adjacent object from being processed by error. Consequently, the processing accuracy can be improved.

Figure 8:
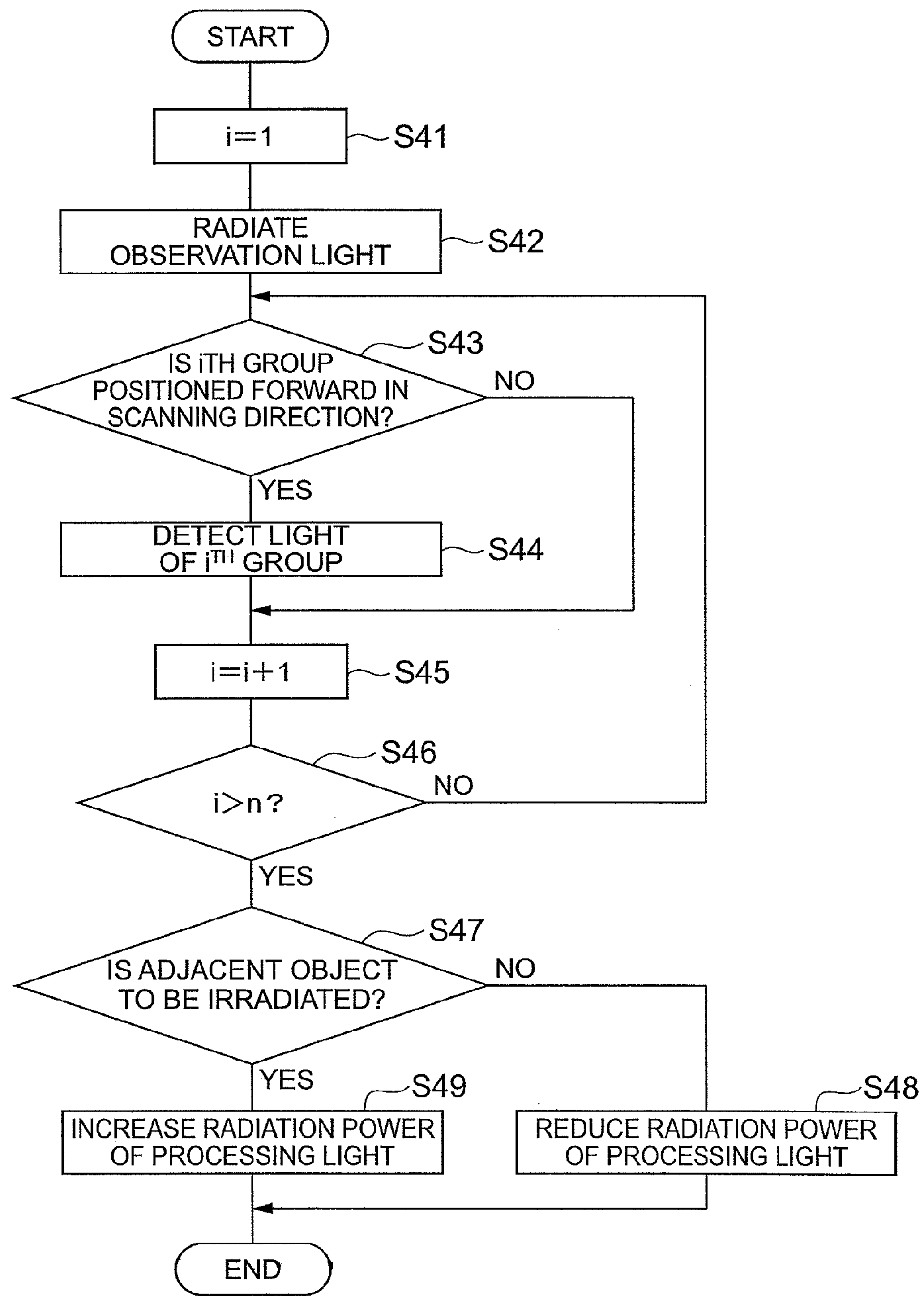
FIG. 8 is a flowchart illustrating a control process of the laser processing apparatus according to the second embodiment.

An alternative processing method using the laser processing apparatus 20 is explained below with reference to FIG. 8. FIG. 8 is a flowchart illustrating a control process of the laser processing apparatus according to the second embodiment.

The control process in FIG. 8 is characterized in that the light generated at the electronic component 2 is detected through the group of the optical fibers 24 disposed forward in the scanning direction of the processing light alone. The control process is repeated by the control unit 31 at a predetermined cycle.

The group number i is first set to 1 (S41). The observation light emitted from the optical fiber 25 is radiated onto the electronic component 2 (S42). It is then determined whether or not the $i^{th}$ (i=1) group is positioned forward in the scanning direction of the processing light (S43). If it is determined that the $i^{th}$ group is not positioned forward in the scanning direction, the light through the optical fibers 24 of the group is not detected, and the process proceeds to S45. If it is determined that the $i^{th}$ group is positioned forward in the scanning direction, the light generated at the electronic component 2 and passing through the optical fibers 24 of the group is detected (S44). Then, an adjacent object is identified based on properties of the detected light.

Subsequently, 1 is added to the original group number i, and thus a new group number i is set (S45). The group number i is compared with a reference value n (S46). If the group number i is equal to or less than the reference value n, the process returns to S43. If the group number i is greater than the reference value n, it is determined whether or not the adjacent object is an object to be irradiated (S47).

If it is determined in S47 that the adjacent object is not to be irradiated, the irradiation power with the processing light is reduced in a process proceeding to the next point (S48). In the process, the control unit 31 transmits, to the processing light source 3, a control signal to reduce the irradiation power; and the processing light source 3 receives the control signal and reduces the power of the generated processing light.

If it is determined that the adjacent object is to be irradiated, the irradiation power with the processing light is increased in a process proceeding to the next point (S49). In the process, the control unit 31 transmits, to the processing light source 3, a control signal to increase the irradiation power; and the processing light source 3 receives the control signal and increases the power of the generated processing light. Thereby, the electronic component 2 is processed. After the process of S48 or S49 is completed, a series of the control process ends. The laser processing method, which identifies only the adjacent object positioned forward in the scanning direction of the processing light, contributes to an increased processing speed.

(Modification)

Figure 9:
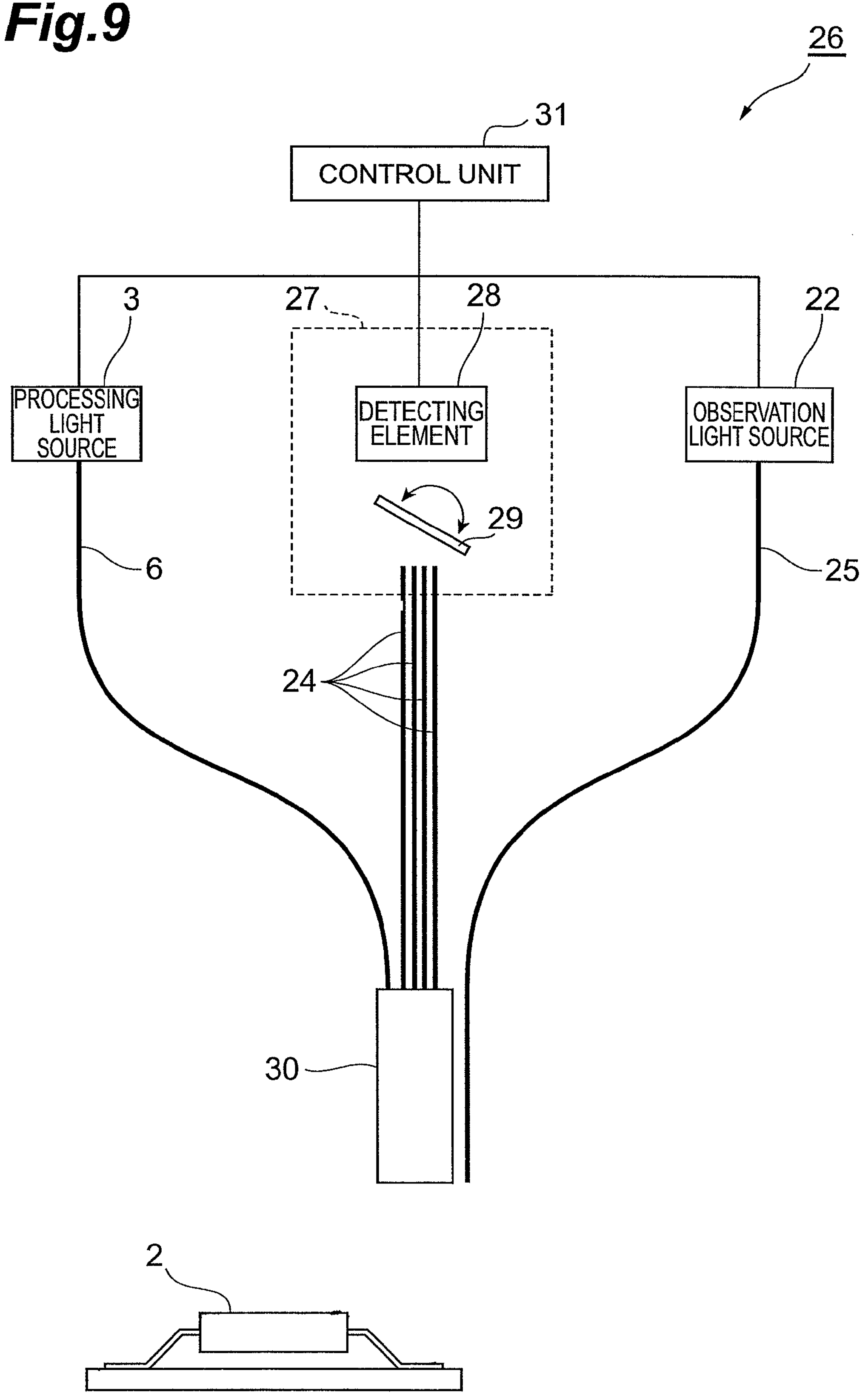
FIG. 9 is a schematic view illustrating a modification of the laser processing apparatus according to the second embodiment.

A modification of the laser processing apparatus 20 according to the second embodiment is explained below. FIG. 9 is a schematic view illustrating a modification of the laser processing apparatus according to the second embodiment. In the modification shown in FIG. 9, a detecting unit 27 of a laser processing apparatus 26 includes a single detecting element 28 and a mirror 29 switching a light path (light path changing means), such that light conducted by the optical fibers 24 enters the detecting element 28. The turnable mirror 29 allows the light conducted by the optical fibers 24 of the four groups to enter the detecting element 28 in sequence. The detecting element 28 can detect light having a plurality of wavelengths, including a wavelength of 445 nm and a wavelength of 660 nm.

The laser processing apparatus 26 having such a configuration provides effects similar to the laser processing apparatus 20 of the second embodiment. In addition, the configuration of the detecting unit 27 can be simplified, thus leading to cost reduction of the apparatus as a whole.

The present invention is by no means limited to the embodiments above. For example, the processing light and the observation light may have the same wavelength. In the embodiments above, the laser processing apparatus and the laser processing method are explained in cases where they are applied in processing of electronic components. In addition to processing of electronic components, the laser processing apparatus and the processing method according to the present invention are also applicable to dental therapy and others.

REFERENCE SIGNS LIST

1, 20, 26 Laser processing apparatus
2 Electronic component (object to be processed)
3 Processing light source (first light emitting unit)
4 Observation light emitting unit (second light emitting unit)
5, 21, 27 Detecting unit
6, 18 Optical fiber (first light guide)
9, 10, 12, 19, 25 Optical fiber (second light guide)
15, 16, 24 Optical fiber (third light guide)
22 Observation light source (second light emitting unit)
29 Mirror (light path changing means)
31 Control unit

The invention claimed is:

1. A laser processing apparatus scanning and processing an object to be processed with processing light, the laser processing apparatus comprising:

a first light emitting unit emitting processing light;
a first light guide conducting the processing light emitted from the first light emitting unit to an object to be processed;
a second light emitting unit emitting observation light that observes the object to be processed;
a plurality of second light guides conducting the observation light emitted from the second light emitting unit to the object to be processed;
a third light guide conducting light having a plurality of wavelengths generated at the object to be processed;
a detecting unit detecting the light having a plurality of wavelengths conducted by the third light guide; and
a control unit controlling a light emitting state of the first light emitting unit, based on a result of detection by the detecting unit, wherein
the second light guides are categorized into at least two groups, and the observation light is conducted by each group in sequence, the observation light being emitted from the second light emitting unit.

2. The laser processing apparatus according to claim 1, wherein the second light guides are categorized into four groups; and
at an emission end of the first light guide, the second light guides categorized into the four groups are disposed a forward direction, a backward direction, left hand, and right hand relative to a scanning direction of the processing light emitted from the first light guide, such that the second light guides surround the first light guide.

3. The laser processing apparatus according to claim 2, wherein the second light guides categorized into the four groups conduct the observation light emitted from the second light emitting unit to the object to be processed.

4. A laser processing apparatus scanning and processing an object to be processed with processing light, the laser processing apparatus comprising:

a first light emitting unit emitting processing light;

a first light guide conducting the processing light emitted from the first light emitting unit to an object to be processed;

a second light emitting unit emitting observation light that observes the object to be processed;

a second light guide conducting the observation light emitted from the second light emitting unit to the object to be processed;

a plurality of third light guides conducting light having a plurality of wavelengths generated at the object to be processed;

a detecting unit detecting the light having a plurality of wavelengths conducted by the third light guides; and a control unit controlling a light emitting state of the first light emitting unit, based on a result of detection by the detecting unit, wherein the third light guides are categorized into at least two groups, and the light is conducted by each group in sequence, the light having a plurality of wavelengths generated at the object to be processed.

5. The laser processing apparatus according to claim 4, wherein the third light guides are categorized into four groups; and at an emission end of the first light guide, the third light guides categorized into the four groups are disposed a forward direction, a backward direction, left hand, and right hand relative to a scanning direction of the processing light emitted from the first light guide, such that the third light guides surround the first light guide.

6. The laser processing apparatus according to claim 5, wherein the third light guides categorized into the four groups conduct the light having a plurality of wavelengths generated at the object to be processed.

7. The laser processing apparatus according to claim 4, wherein the detecting unit comprises a detecting element corresponding to each group of the third light guides.

8. The laser processing apparatus according to claim 4, wherein the detecting unit comprises:

a single detecting element; and light path changing means allowing the light conducted by the third light guides to enter the detecting element.

9. A laser processing method using the laser processing apparatus according to claim 1, the laser processing method comprising:

(1) irradiating the object to be processed with the observation light from every group of the second light guides;

(2) detecting the light having a plurality of wavelengths generated at the object to be processed, and identifying the object as an object to be irradiated or not, based on properties of the detected light; and (3) controlling the processing light based on a result of identification of the object to be irradiated, and processing the object.

10. The laser processing method according to claim 9, wherein, in step (1), the group of the second light guides disposed forward in the scanning direction of the processing light is used alone to radiate the observation light onto the object to be processed.

11. A laser processing method using the laser processing apparatus according to claim 4, the laser processing method comprising:

(1) irradiating the object to be processed with the observation light;

(2) detecting the light having a plurality of wavelengths generated at the object to be processed, using each group of the third light guides, and identifying the object as an object to be irradiated or not, based on properties of the detected light; and (3) controlling the processing light based on a result of identification of the object to be irradiated, and processing the object.

12. The laser processing method according to claim 11, wherein, in step (2), the group of the third light guides disposed forward in the scanning direction of the processing light is used alone to detect the light having a plurality of wavelengths generated at the object to be processed.

13. The laser processing apparatus according to claim 5, wherein the detecting unit comprises a detecting element corresponding to each group of the third light guides.

14. The laser processing apparatus according to claim 6, wherein the detecting unit comprises a detecting element corresponding to each group of the third light guides.

15. The laser processing apparatus according to claim 5, wherein the detecting unit comprises:

a single detecting element; and light path changing means allowing the light conducted by the third light guides to enter the detecting element.

16. The laser processing apparatus according to claim 6, wherein the detecting unit comprises:

a single detecting element; and light path changing means allowing the light conducted by the third light guides to enter the detecting element.

17. The laser processing apparatus according to claim 4, wherein the detecting unit comprises a kind of detecting element corresponding to each group of the third light guides.

18. The laser processing apparatus according to claim 5, wherein the detecting unit comprises a kind of detecting element corresponding to each group of the third light guides.

19. The laser processing apparatus according to claim 6, wherein the detecting unit comprises a kind of detecting element corresponding to each group of the third light guides.

* * * * *